Figure 1:
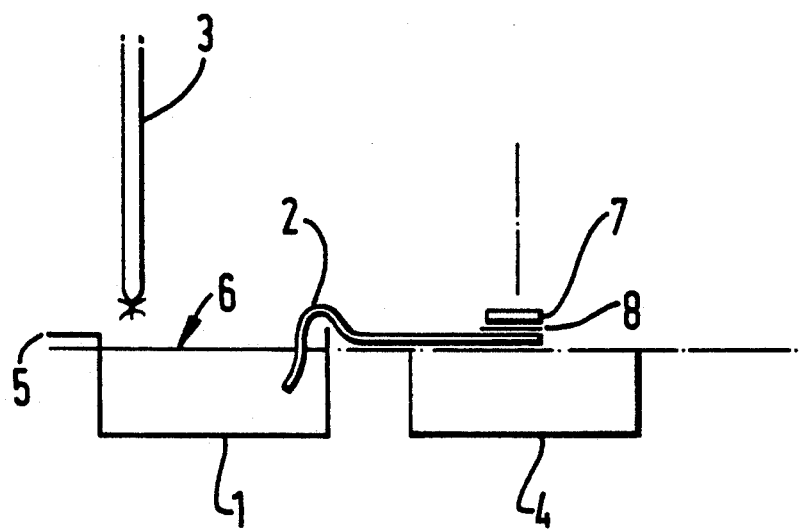

United States Patent [19]
Mahoney

[11] Patent Number: 5,256,477
[45] Date of Patent: Oct. 26, 1993

[54] ABSORBENCY ALGINATE FABRIC, USE AS WOUND AND BURN DRESSINGS, AND A METHOD FOR ITS PREPARATION

[75] Inventor: Peter M. J. Mahoney, Llys Berwyn, Wales

[73] Assignee: BritCair Limited, Aldershot, England

[21] Appl. No.: 760,297

[22] Filed: Sep. 16, 1991

[51] Int. Cl.⁵ .......................... B32B 5/16; B32B 3/26; A61F 13/15
[52] U.S. Cl. ........................ 428/283; 28/107; 428/288; 428/289; 428/292; 428/311.1; 428/311.5; 604/358; 604/360; 604/367; 604/383
[58] Field of Search ............... 428/224, 234, 284, 288, 428/292, 293, 300; 28/107

[56] References Cited
U.S. PATENT DOCUMENTS 4,199,644  4/1980  Platt .
4,277,531  7/1981  Picone .................. 28/107
4,948,649  8/1990  Hiers et al. ............ 28/107

FOREIGN PATENT DOCUMENTS 0344913   6/1989   European Pat. Off. .
653341    5/1951   United Kingdom .
8900706   12/1989  United Kingdom .
90/01954  3/1990   World Int. Prop. O. .

*Primary Examiner*—George F. Lesmes
*Assistant Examiner*—James D. Withers
*Attorney, Agent, or Firm*—Joseph F. DiPrima; Richard S. Parr

[57] ABSTRACT

A non-woven fabric of alginate staple fibres, characterized in that the absorbency of the fabric is greater than 25.0 grams of deionised water or 19.0 grams of saline water per gram of fabric as measured with reference to the test method depicted in FIG. 1, is prepared by a modified needle-tacking process. The fabric is useful for the preparation of wound and burn dressings.

11 Claims, 1 Drawing Sheet

ABSORBENCY ALGINATE FABRIC, USE AS WOUND AND BURN DRESSINGS, AND A METHOD FOR ITS PREPARATION

The present invention relates to an alginate fabric. More particularly, the invention concerns wound or burn dressing formed from a non-woven fabric of alginate fibres which has high absorbency and good integrity.

Alginate fibres have been known for some time as being useful in the preparation of surgical dressings. For example, United Kingdom Patent No. 653341, published in 1951, describes surgical dressings formed from fibres of calcium alginate. Even then, however, it was known that a failing of calcium alginate fibres is their relative insolubility in water or wound exudate matter. Bonniksen in GB-A-653341 therefore proposed that a proportion of the calcium ions in calcium alginate be replaced by sodium cations, since sodium alginate was known to be more soluble than calcium alginate. The resulting process has become known as "conversion" of calcium alginate to form a mixed salt alginate.

Various types of dressing formed from fabrics comprising alginate fibres are known. For example, Sorbsan surgical dressing is a carded web of layered alginate fibres, and Kaltostat haemostatic wound dressing is a carded and needle-tacked web of alginate fibres.

EP-A-0344913 describes an alginate wound dressing of an integrity alleged to be such as to enable it to be lifted in one piece from a wound even when saturated with blood or other saline fluids. This is stated to be achievable at basis weights as low as 50 g/m$^2$. Briefly, the wound dressing provided by EP-A-0344913 comprises a non-woven fabric of alginate staple fibres, the fabric being substantially free from any adhesive binder or of interfusing of fibres at their crossing points. Nevertheless, at basis weights below 50 g/m$^2$, the inclusion of reinforcing fibres such as rayon into the wound dressing is provided for. The required integrity is imparted to the dressing fabric of EP-A-0344913 by subjecting the non-woven web of staple alginate fibres to a hydraulic entanglement procedure which preferably comprises hydroentanglement.

Where a wound is exuding heavily, the two essential desiderata for an ideal dressing are good integrity and high absorbency. Good integrity ensures that the dressing is easy to handle. High absorbency means that an efficient uptake of exudate, together with its associated toxins and other undesirable matter, can be achieved.

Although the Sorbsan product identified above has a moderately high absorbency, it does however have a tendency to disintegrate when wet, thereby giving rise to handling problems both in application to and removal from the wound.

Whilst the wound dressing provided by EP-A-0344913 is unquestionably of good integrity (cf. for example the results obtained for Dry Web Strength and Wet Web Strength in Table III of EP-A-0344913), its absorbency, as measured by its serum uptake in g/cm$^2$, is at best only approximately 50% that of a prior art wound dressing as exemplified by Kaltostat carded and needle-tacked web (compare the serum uptake results obtained for Examples 13 and C3 in Table III of EP-A-0344913). An example of an alginate fabric in accordance with EP-A-0344913 is the commercially available Tegagel.

We have now found that a non-woven fabric of alginate fibres can be prepared which can be formed into a wound or burn dressing whose integrity is comparable to that of the commercially-available Kaltostat dressing but which possesses a saline absorbency approximately 33% greater than that of Kaltostat and at least 40% greater than that of Sorbsan. Moreover, unlike Sorbsan, the dressing of the invention remains intact when wet, thereby minimising handling problems.

It is believed that the surprisingly elevated absorbency of the fabric prepared by the method of the invention arises by virtue of its open-textured structure, resulting in a greatly increased capillarity than can be achieved with a more compressed fabric such as Sorbsan, or with a wet-laid (or "hydroentangled") alginate fabric such as Tegagel. It is believed in turn that an increased capillarity is advantageous in that it permits a more rapid access of hydrophilic substances, and thus an enhanced uptake of wound exudate, than can be achieved with the fabrics used in the manufacture of the prior art dressings.

The present invention accordingly provides a fabric of alginate fibres, characterised in that the absorbency of the fabric is greater than 25.0 grams of deionised water per gram of fabric as measured with reference to the test method depicted in FIG. 1 appended hereto.

In a further or alternative aspect, the present invention provides a fabric of alginate fibres, characterised in that the absorbency of the fabric is greater than 19.0 grams of saline water per gram of fabric as measured with reference to the test method depicted in FIG. 1 appended hereto.

In a preferred embodiment, the alginate fabric of the present invention is a non-woven fabric of alginate staple fibres.

The conventional needle-tacking procedure, as employed for example in the preparation of Kaltostat haemostatic dressing identified above, comprises piercing a carded and layered mat or web of alginate fibres with an array of barbed needles such that the fibres in each layer become entangled. Each needle is generally furnished with a multiplicity of barbs, typically ten. Thus, the mat is essentially held together by entanglement of the fibres of a given layer with those of the layers above and below. In the conventional procedure, at least one of the barbs on each barbed needle enters through one surface of the mat, penetrates completely through the various layers thereof, and emerges through the opposite surface of the mat before being withdrawn again through the first surface. This results in a fabric having a substantially compressed or "flat" appearance owing to the high degree of entanglement of the individual fibres within its structure.

Clearly, if only one barb per needle penetrates completely through all the layers of the mat, this will be the barb closest to the tip of the needle. This barb is referred to hereinafter as the "leading" barb.

We have now found that the alginate fabric according to the present invention can suitably be prepared by a modification of the conventional needle-tacking procedure. In a further aspect, therefore, there is provided a method of preparing the alginate fabric according to the invention which comprises the following steps:

(1) processing alginate fibres to provide a mat; and (2) entangling the fibres in the mat by means of barbed needles which (a) enter through one surface of the mat; (b) pierce through the mat such that the leading barb penetrates to a depth of from about 60 to about 99% of the thickness of the mat; and (c) are subsequently withdrawn through the first surface of the mat.

It will be appreciated that, in the above-described method of the invention, the leading barb on each barbed needle does not penetrate completely through the mat during processing. By virtue of this fact, the resulting fabric is appreciably less "flat" or compressed than the known Kaltostat and Sorbsan dressings, having a more "downy" appearance and feel when dry. In order to ensure that an alginate fabric having the desired properties is reliably obtained, the depth to which the leading barb on each needle pierces through the mat of alginate fibres will ideally be maintained as required at between 60 and 99% of the thickness of the mat. Preferably, the needles will be set such that the leading barb on each needle pierces through the mat to a depth of between 65 and 85% of the thickness of the mat. In a particularly favoured embodiment, the depth to which the leading barb on each needle pierces through the mat is approximately 75% of the thickness of the mat.

The present invention further provides an alginate fabric comprising a mat of alginate fibres wherein the fibres are entangled through from 60 to 99% of the thickness of the mat, preferably from 65 to 85% of the thickness of the mat, most preferably about 75% of the thickness of the mat.

It will be apparent from the above description that a critical factor in determining the quality of the finished alginate fabric is the depth to which the leading barb on each needle pierces through the layers of the mat during processing. However, it has been found that the quality of the finished fabric is also affected by the frequency of needling, i.e. the number of needles resident in the needle board per unit area. Hence, depending upon the quality of finished alginate fibre desired, an appropriate needling frequency can be selected having regard to the depth at which the needles have been set to pierce through the mat, and vice versa. In general, a balance between these two factors can be readily achieved on the basis of trial and error.

For most applications, a needling frequency of between 10,000 and 40,000 needle penetrations per square meter will be appropriate. In a typical configuration, a needling frequency of 26,000 needle penetrations per square meter can be employed.

Suitable alginates for use in the preparation of fibres according to the invention include both water-soluble and water-insoluble alginates, but will preferably be water-soluble alginates. A particular water-soluble alginate for use in the invention is sodium alginate. Nevertheless, the sodium alginate may advantageously contain up to 1.5% by weight of calcium ions. Examples of specific sodium alginate products of use in the invention include Manucol DM, which is available from Kelco International Limited, and Protan LF 10/60, which is available from Protan Limited.

Conveniently the alginate fabric according to the invention may be prepared from calcium alginate or mixed calcium/sodium alginate fibres. Preferably the alginate fabric according to the invention will be prepared from mixed calcium/sodium alginate fibres wherein the ratio of calcium to sodium cations is in the range of 40:60 to 90:10, more preferably, about 80:20.

In the above-described method of preparing the alginate fabric according to the invention, a cotton card may suitably be used to form a web, which may then be cross-lapped, for example with a Garnet Bywater cross-lapper, to provide a layered mat. Needle punching may conveniently be effected in a Garnet Bywater needle loom with the needles set to pierce through the layers of the alginate fibre mat to an appropriate depth.

The number of layers within the mat is not critical, and will generally depend upon the basis weight of fabric desired.

The basis weight of a given fabric will in general be dependent upon the use, for example as a wound or burn dressing, to which the fabric is to be put. By way of example, for a moderately exuding wound, a basis weight in the region of 120 $g/m^2$ is indicated. Similarly, for a heavily exuding wound, a basis weight in the region of 240 $g/m^2$ is indicated. Accordingly the alginate fibre mat will suitably comprise between 5 and 300 layers, preferably between 15 and 55 layers and especially between 30 and 40 layers. It is estimated that a square meter of a 36-layer fabric prepared by the method of the invention has a total fibre surface area of at least 50 square meters. It is not essential that the mat should comprise a plurality of layers. Where the mat does not have a layered structure, clearly the thickness and density of the mat as well as the dimensions of the fibre, will be determinative of basis weight.

It will be appreciated that basis weights of less than 120 $g/m^2$ and greater than 240 $g/m^2$ can be achieved, for example by varying the number of layers or thickness of the mat, or the dimensions of the fibre. For example, the basis weight of fabric according to the invention will suitably be in the range of 80 $g/m^2$ to 1000 $g/m^2$, preferably between 160 $g/m^2$ and 350 $g/m^2$, for example between 160 $g/m^2$ and 200 $g/m^2$, but most preferably about 240 $g/m^2$.

In another aspect, the present invention provides a wound dressing comprising a fabric of alginate fibres according to the present invention.

Preferably, the wound dressings according to the invention will comprise a non-woven fabric of alginate staple fibres.

As used herein, the expression "wound dressing" includes surgical dressings. The term "wound" includes cut, sore, ulcer, blister, rash or any other lesion or area of troubled skin.

The fabric prepared by the method according to the invention has been found to have a water-retention capacity in the region of 30 times its own weight of water. Thus, in view of its high absorbency and considerable water-retention capabilities, the alginate fabric of the invention may also be advantageously adapted for use as a burn dressing. By way of comparison, the commercially available burn dressing Water.Jel, which is based on wool and obtainable from Trilling Medical Technologies, Inc., is stated in its product literature to possess a water-retention capacity of only 13 times its own weight. The Water.Jel product is the subject of U.S. Pat. No. 3,902,559.

In a further aspect, therefore, the invention provides a burn dressing comprising a fabric of alginate fibres according to the present invention.

Preferably, the burn dressing according to the invention will comprise a non-woven fabric of alginate staple fibres.

As used herein, the term "burn" includes burn, scald and the like.

In the management of burns, the affected site is desirably kept continually moistened, since it has been observed that an extremely effective treatment for burns is to allow cool water to penetrate over a prolonged period to the layers of skin underlying the affected area. It is accordingly envisaged that the burn dressing of the present invention would be applied in a wetted state, either with pure water or preferably with saline water, to the site of the burn. The high absorbency of the fabric of the invention will ensure that an appreciable supply of water is available from the wetted burn dressing, whilst the water-retention lo capabilities of the fabric of the invention will assist in prolonging the release of cooling water to the affected area. A further advantage of the fabric of the invention when adapted for use as a burn dressing is that it does not drip when applied to a curved surface such as an area of the human body, in contrast to conventional burn dressings such as surgical gauze and cotton wool which have a propensity to allow water to "run off".

The burn dressing of the invention may suitably be supplied in a pre-wetted state, or alternatively may be supplied in the dry state with instructions for wetting before application to the affected area in the eventuality of a burn. If supplied in a pre-wetted state, the burn dressing will advantageously incorporate conventional preservatives, for example Metasol D3T (Merck), Parasept (methyl paraben) (Kaloma Chemical) or Bromopol (2-bromo-2-nitro-1,3-propanediol) (Boots Ltd.), in order to prevent or retard the biological degradation of the fabric constituents.

In order to enhance its absorbency and water-retention capability, the burn dressing of the invention may advantageously incorporate additional gel-forming constituents, in particular a bio-gum such as gellan gum or locust bean gum. This would ensure not only that more cooling water were available for administration to the affected site, but also most notably that its duration of release were significantly prolonged.

In order to enhance its efficacy in the treatment of burns, the burn dressing of the invention may advantageously incorporate known antimicrobial agents which will serve to prevent or inhibit infection at the affected site. Such antimicrobial agents suitably include silver sulfadiazine, zinc salts, metronidazole and chlorhexidine.

The wound or burn dressings formed from the alginate fabric according to the present invention will advantageously be conventional dressings well known in the art. Examples of suitable dressings include bandages, adhesive strip dressings, island dressings, pads of various kinds, surgical sponges and packs, ward dressings, and such articles as tampons which may, for example, be impregnated with an antifungal agent such as miconazole for the treatment of candidal vaginitis (vaginal thrush). Such dressings may conveniently be prepared by standard methods known from the art.

The dressings in accordance with the present invention will conveniently be packaged in a hermetically-sealed envelope and sterilised, e.g. with ethylene oxide or by gamma-irradiation.

The following non-limiting Example is intended to illustrate the present invention.

PREPARATION 1 OF WO-A-90/01954

6.6 kg (6.0 kg bone dry) of sodium alginate powder was dissolved in 100 dm$^3$ of demineralized water containing sodium hypochlorite (60 g available chlorine) using a high speed stirrer. The excess chlorine is reduced to 25 ppm by the addition of sodium sulfite and the resultant solution was filtered to remove incompletely dissolved material. The solution was then spun through a viscose type spinning jet into a spin bath containing 1% calcium chloride and a sufficient quantity of cetyl pyridinium chloride (a quaternary ammonium wetting agent) to prevent fiber adhesion. After stretching the fibers in a steam chamber, the yarn is washed free from spin bath liquors in a conventional wash bath system, dried and collected either in a box or on a cheese winder.

EXAMPLE 1

Calcium sodium alginate fibre, prepared as described in Preparation 1 of WO-A-90/01954, is crimped and cut to 50 mm lengths. Approximately 5 kg of cut tow is placed in a hopper connected to the textile equipment and regularly replenished. From the hopper, approximately 208 g of tow is fed into a carding machine every 105 seconds, producing a fine combed alginate web. A cross-lapper is set at approximately 10 laps per minute to produce 66 cm-wide layers. The layered web is fed into a standard needle loom fitted With $15 \times 18 \times 32 \times 3$ csp specification needles (obtainable from Foster Needles), set such that the leading barb on each needle pierces through the web to a depth of approximately 75% of the thickness of the web, and operating at 156 strokes per minute. The resulting needle felt is slit to an appropriate width using crush cutting blades, and wound at approximately 0.7 meters per minute.

TEST METHOD

The apparatus used in the determination of absorbency is depicted in FIG. 1, and consists of water bath 1-containing a 0.9% (w/w) aqueous saline solution, or deionised water, absorbent strip 2, burette 3, top-pan balance-4- and overflow 5.

The thickness of the absorbent strip 2 is substantially equivalent to that of the dressing 7. The filter paper 8 has substantially the same planar dimensions as the dressing 7, but not necessarily the same thickness.

The apparatus is set up with the surface 6 of the saline solution or water level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 1. The balance 4 is then tared. A weighed dressing 7 and filter paper 8 (cut to size) is positioned as depicted in FIG. 1. Care must be taken to ensure that the edge of the absorbent strip 2 furthest away from the water bath 1 does not extend beyond the corresponding edge of the dressing 7, as shown in FIG. 1.

After six minutes the weight shown on the balance 4 is recorded. The dressing 7 and filter paper 8 are then removed and any residual weight on the balance 4 noted.

Absorbency is determined on the basis of the following equation:

$$\text{wt. of liquid absorbed} = \text{total wt. on balance} - \begin{bmatrix} \text{dry wt. dressing } + \\ \text{wt. of satd. filter paper } + \\ \text{residual wt. on balance} \end{bmatrix}$$

RESULTS

Using the test method described above, the saline absorbencies of the fabric according to the invention, and of commercially available Kaltostat dressing, were determined and compared. In the former case ten samples, and in the latter case twelve samples, of the fabric were taken and an average value for the absorbency was calculated. The results obtained were as follows:

TABLE I

Alginate fabric of Example 1

| Wt. of dressing (g) | Wt. of saline absorbed (g) | Wt. of saline absorbed per gram of dressing (g) |
|---|---|---|
| 0.4983 | 10.10 | 20.26 |
| 0.5237 | 11.00 | 21.00 |
| 0.4900 | 10.30 | 21.02 |
| 0.6130 | 13.40 | 21.85 |
| 0.5157 | 10.90 | 21.14 |
| 0.4900 | 9.80 | 20.00 |
| 0.6128 | 12.90 | 21.05 |
| 0.5400 | 11.70 | 21.67 |
| 0.5934 | 12.20 | 20.56 |
| 0.6300 | 13.20 | 20.95 |

TABLE II

Kaltostat

| Wt. of dressing (g) | Wt. of saline absorbed (g) | Wt. of saline absorbed per gram of dressing (g) |
|---|---|---|
| 0.3282 | 4.729 | 14.41 |
| 0.2311 | 3.637 | 15.74 |
| 0.2573 | 3.886 | 15.19 |
| 0.3098 | 4.749 | 15.33 |
| 0.2466 | 4.120 | 16.71 |
| 0.2583 | 4.300 | 16.65 |
| 0.3107 | 5.110 | 16.45 |
| 0.3212 | 4.959 | 15.44 |
| 0.2784 | 4.420 | 15.88 |
| 0.2978 | 4.535 | 15.23 |
| 0.3106 | 5.000 | 16.10 |
| 0.3100 | 4.904 | 15.82 |

From Table I above, it can be calculated that the average saline absorbency of the alginate fabric of Example 1 is 20.95 g of saline per gram of dressing; whereas, from Table II, the average absorbency of commercial Kaltostat can be calculated to be 15.75 g of saline per gram of dressing. In other words, the alginate fabric of Example 1 is, on average, approximately 33% more saline absorbent than the commercial Kaltostat dressing.

Using the same test method, the water absorbencies of the fabric according to the invention and of Kaltostat were determined and compared. The results obtained were as follows:

TABLE III

Alginate Fabric of Example 1

| Wt. of dressing (g) | Wt. of deionised water absorbed (g) | Wt. of deionised water absorbed per gram of dressing (g) |
|---|---|---|
| 0.5912 | 16.40 | 27.74 |
| 0.5345 | 17.10 | 31.99 |
| 0.4987 | 14.30 | 28.67 |
| 0.5113 | 13.82 | 27.03 |
| 0.6002 | 18.20 | 30.32 |
| 0.4580 | 12.60 | 27.51 |
| 0.5160 | 12.90 | 25.00 |
| 0.4328 | 13.50 | 31.19 |
| 0.4790 | 12.80 | 26.72 |
| 0.6869 | 17.90 | 28.15 |

TABLE IV

Kaltostat

| Wt. of dresing (g) | Wt. of deionised water absorbed (g) | Wt. of deionised water absorbed per gram of dressing (g) |
|---|---|---|
| 0.2638 | 5.54 | 20.99 |
| 0.2616 | 5.70 | 21.17 |
| 0.3259 | 6.37 | 19.56 |
| 0.2862 | 6.11 | 21.36 |
| 0.3486 | 7.35 | 21.09 |
| 0.2644 | 5.54 | 20.94 |
| 0.2861 | 6.11 | 21.37 |
| 0.2630 | 5.44 | 20.67 |
| 0.3546 | 7.15 | 20.15 |

From Table III above, it can be calculated that the average deionised water absorbency of the alginate fabric of Example 1 is 28.43 g of deionised water per gram of dressing; whereas, from Table IV, the average deionised water absorbency of commercial Kaltostat can be calculated to be 20.81 g of deionised water per gram of dressing. That is to say, the alginate fabric of Example 1 is, on average, approximately 36% more absorbent of deionised water than is Kaltostat.

We claim:

1. A non-woven fabric of alginate staple fibers comprising a mat of alginate staple fibers wherein said fibers are entangled through from 60% to 99% of the thickness of said mat, wherein the absorbency of the fabric is greater than 25.0 grams of deionized water per gram of fabric, said absorbency determined by contacting the fabric with a first end of a water absorbent strip, wherein a second end of the water absorbent strip contacts a deionized water source.

2. A fabric according to claim 1 which comprises a non-woven fabric of alginate staple fibres.

3. A fabric according to claim 1 wherein said fibres are entangled through from 65% to 85% of the thickness of said mat.

4. A fabric according to claim 3 wherein said fibres are entangled through about 75% of the thickness of said mat.

5. The fabric according to claim 1 comprising mixed calcium/sodium alginate fibres wherein the ratio of calcium cations to sodium cations is in the range of 40:60 to 90:10.

6. The fabric according to claim 1 the basis weight whereof is in the range of about 160 g/m$^2$ to about 350 g/m$^2$.

7. A wound dressing comprising the fabric of alginate fibres according to claim 1.

8. A burn dressing comprising the fabric of alginate fibres according to claim 1.

9. The burn dressing according to claim 8 comprising an antimicrobial agent.

10. A non-woven fabric of alginate staple fibers comprising a mat of alginate staple fibers wherein said fibers are entangled through from 60% to 99% of the thickness of said mat, wherein the absorbency of the fabric is greater than 19.0 grams of saline water per gram of fabric, said absorbency determined by contacting the fabric with a first end of a water absorbent strip, wherein a second end of the water absorbent strip contacts a saline water source.

11. An improvement in a non-woven fabric of alginate staple fibres wherein the improvement consists of entanglement of the fibres through from 60% to 99% of the thickness of the mat whereby the absorbency of the fabric is increased to greater than 25 grams of deionised water per gram of fabric.

* * * * *